May 9, 1972 J. M. GARABEDIAN Plant Pat. 3,164
PLUM TREE
Filed Oct. 19, 1970
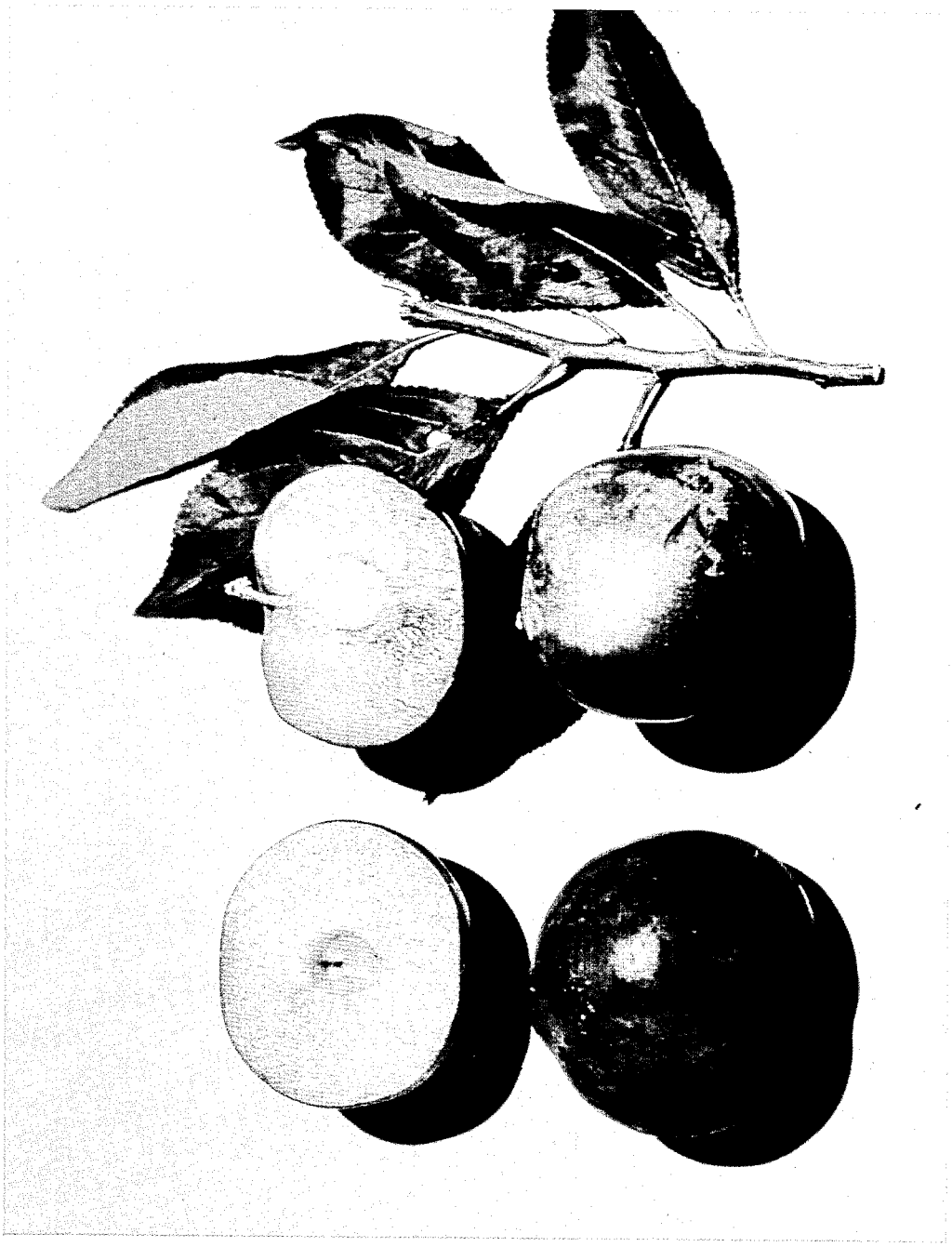
INVENTOR
John M. Garabedian
BY
Webster & Webster
ATTORNEYS

United States Patent Office

Plant Pat. 3,164
Patented May 9, 1972

3,164
PLUM TREE

John M. Garabedian, 3158 Hamilton St., Fresno, Calif. 93712

Filed Oct. 19, 1970, Ser. No. 82,228
Int. Cl. A01h 5/03
U.S. Cl. Plt.—38 1 Claim

ABSTRACT OF THE DISCLOSURE

A plum tree of medium to small size, medium vigor, upright, open, vase-formed, hardy, and a regular and productive bearer of uniform, large to medium size, usually semi-freestone fruit having red skin and red flesh.

ORIGIN OF THE VARIETY

The present variety of plum tree was originated by me in the manner below described.

A quantity of seeds were gathered from open-pollinated hybrids of the Queen Ann (unpatented) and Elephant Heart (unpatented); the trees, from which said seeds were obtained, existed in an orchard on a ranch (of which I am an owner) located in Madera County, Calif. The seeds, as thus gathered, were planted in a nursery plot on a ranch (of which I am also an owner) in Fresno County, Calif. The resultant seedling—which were open-pollinated—were maintained by me under close and careful observation, and—at fruiting age—one of such seedlings, which is the present variety, evidenced certain novel and commercially desirable characteristics. The variety was, therefore, selected by me for asexual reproduction and in anticipation of ultimate commercial growing.

ASEXUAL REPRODUCTION OF THE VARIETY

After its origination, as above, I asexually reproduced the present variety of plum tree by budding on several Casselman (unpatented) trees growing on the aforesaid ranch in Fresno County, Calif.; such reproductions, in maturity, having run true to the original tree in all respects.

SUMMARY OF THE VARIETY

The present variety of plum tree is of medium to small size, medium vigorous, upright, open, vase-formed, hardy, and a regular and productive bearer of uniform, large to medium size, usually semi-freestone fruit having red skin and red flesh; the variety being particularly characterized, as to novelty, by fruit which, in comparison to the Santa Rosa (unpatented), sizes more readily, ripens approximately seven to ten days earlier, is more uniform in size and color, and has firmer flesh which enhances its shipping quality and assures longer shelf life.

BRIEF DESCRIPTION OF THE DRAWING

The drawing is an illustration, by photographic reproduction in color, of a twig with leaves, and individual fruit; one of the latter being cut in half to expose the flesh, and with the stone remaining in one half of such cut fruit.

DESCRIPTION OF THE VARIETY

The botanical details of this new and distinct variety of plum tree—with color definitions (except those in common color terms) referenced to Maerz and Paul Dictionary of Color—are as follows:

Tree:
- *Size.*—Medium to small.
- *Vigor.*—Medium.
- *Growth.*—Upright.
- *Density.*—Open.

- *Form.*—Vase-formed.
- *Hardiness.*—Hardy.
- *Production.*—Productive.
- *Bearing.*—Regular bearer.

Trunk:
- *Size.*—Medium.
- *Texture.*—Medium.
- *Bark pattern.*—Vertical striations.
- *Color.*—Light gray over sepia (8–A–10).

Branches:
- *Size.*—Medium.
- *Texture.*—Medium.
- *Color.*—Current season's growth—dorsal side—Tapestry red (7–J–5)—ventral side—Biscay green (21–K–5 to 21–K–7). Two-year wood—dorsal side—Bonito grey (7–A–7)—ventral side—Montella brown (8–J–11).
- *Bark pattern.*—Vertical striations; more abundant on ventral side. Lighter on two-year and older wood.
- *Lenticels.*—Number—numerous. Size—small.

Leaves:
- *Size.*—Medium—length—7.5 to 10 cm., average 8.4 cm.—width—3.0 to 4.8 cm., average 3.9 cm.
- *Form.*—Oblanceolate, few elliptical—acuminate, few acute.
- *Thickness.*—Thin.
- *Color.*—Dorsal side—Yew green (24–L–4 to 24–L–9)—ventral side—Elm green (23–J–5 to 23–L–7).
- *Leaf base.*—Broadly acute, few acute to obtuse.
- *Leaf veins.*—Pinnately net-veined.
- *Margin.*—Glandular; crenate.
- *Petiole.*—Length—medium—10 to 16 mm., average 13.2 mm. Thickness—medium. Color—dorsal side — Rhododendron red (54–H–6) — ventral side—Leek green (22–J–5).
- *Glands.*—Number—2 to 7, average 4.1; usually opposite; small; usually reniform; red, few green; positioned mostly on petiole at base of blade.
- *Stipules.*—1 to 2; length—mostly ⅜″ on current season's growth.
- *Leaf buds.*—Small; pointed.

Flower buds:
- *Hardiness.*—Hardy.
- *Size.*—Small—average before opening—6 mm. x 7 mm.
- *Length.*—Short.
- *Form.*—Pointed; plump; free.
- *Surface.*—Glabrous.
- *Location.*—Lateral on spurs.
- *Development.*—Good on one-year wood.
- *Color (pre-bloom).*—Advanced popcorn stage—white.

Flowers:
- *Blooming period.*—Date of first bloom—Feb. 18, 1970. Date of full bloom—Feb. 28, 1970; medium, as compared with other varieties; about with Nubiana (unpatented); after Burmosa (unpatened).
- *Size.*—Medium to small.
- *Color.*—White.
- *Calyx lobes.*—Color—Lettuce green (20–L–5).
- *Stamen pedicel.*—Color—Lettuce green (20–L–5).
- *Calyx cup.*—Inside color—Windsor tan (13–F–12).
- *Sepal.*—Length—Short—average 3.5 mm. Width—average 2 mm.
- *Pedicel.*—Length—medium to short—average 7 mm.
- *Petals.*—Small; round; some with fluted or ruffled edges.
- *Anthers.*—Number—fully developed—18 to 33, average 23. Color—Spruce yellow (12–J–9).

*Pistils.*—At full bloom of blossoms 30% abortive; open one or two days 50% abortive.

Fruit:

*Maturity when described.*—Eating hard (June 12, 1969).

*Date of first picking.*—June 12, 1969.

*Date of last picking.*—June 17, 1969.

*Date of picking compared to another variety.*—7–10 days before Santa Rosa.

*Size.*—Uniform; large to medium—diameter axially—1½" to 2", average 1⅞"—transversely in suture plane—1½" to 1⅞", average 1¾".

*Form.*—Uniform; usually slightly unsymmetrical; globose to oblate; longitudinal form through suture; round-oblate slightly truncated at base and at apex.

*Suture.*—Distinct; shallow; extends from base to apex.

*Ventral surface.*—Rounded slightly to strongly.

*Lips.*—Lipped toward both sides; equal.

*Cavity.*—Rounded; short and deep; elongated in suture plane with suture showing on one side—depth—¼" to ½", average ⅜"—breadth—½" to ⅝", average ½"—markings—some russet areas.

*Base.*—Rounded to truncate, usually the latter.

*Apex.*—Truncate; depressed.

*Pistil point.*—Mostly apical (many oblique); apex to side away from suture.

*Stem.*—Medium—length—12–220 mm., average 15 mm.—width—average 2 mm.

Skin:

*Thickness.*—Medium, few thick.

*Texture.*—Medium.

*Tenacity.*—Tenacious to flesh.

*Tendency to crack.*—None in dry season.

*Color.*—Bokhara red (47–L–5) shading deeper to Spanish raisin (48–L–8). Many light dots. Davy's grey (47–A–6) bloom.

Flesh:

*Color.*—Algerian red (7–L–5) to Cardinal red (5–L–5) with yellowish tinge near cavity; few streaked and mottled with red next to skin. In full maturity, all flesh is red.

*Amygdalin.*—Wanting.

*Juice.*—Moderate; rich.

*Texture.*—Firm; fine; melting.

*Fibers.*—Few; fine; tender.

*Ripens.*—Slightly unevenly; earliest at apex along both lips.

*Flavor.*—Mild; delicate to vinuous; slightly acid directly under skin.

*Aroma.*—Very slight.

*Eating quality.*—Very good.

Stone:

*Type.*—Semifree, few cling; usually breaks free with minimum maturity; on ripe fruit, a section of flesh may adhere to side of stone near apex.

*Size.*—Medium to small—length—17–22 mm., average 18 mm.—breadth—15–16 mm., average 15.3 mm.—thickness—8–10 mm., average 9.6.

*Form.*—Oblong—oval, few obovoid.

*Base.*—Slightly oblique.

*Hilum.*—Narrow; oblong; small.

*Apex.*—Rounded, tip pointed.

*Sides.*—Equal, few unequal, curved on right side.

*Surface.*—Irregularly furrowed near base; rough granular with more ridges and grooves at base end, mostly smooth on both sides near apex tip.

*Ridges.*—Rounded, few jagged; extends from base to apex; on either side—continuous.

*Pits.*—Small; angular; uneven; irregular.

*Ventral edge.*—Thin, with wing toward apex.

*Dorsal edge (on suture side).*—Full, with shallow medium broad groove throughout.

*Color.*—Light cream (9–D–3).

*Tendency to split.*—None in dry season.

*Kernel.*—Ovoid, pointed; bitter; test sample—55% of seed viable—average width—9 mm.—average length—12 mm.—average thickness—5 mm.—surface strippled or etched in appearance.

*Seed coat.*—Pellicle—Harvest brown (12–E–9), with darker striations. Amygdalin—kernel taste indicates presence.

Use: Dessert.

Keeping quality: Good.

Shipping quality: Good.

The plum tree and its fruit herein described may vary in slight detail due to climatic and soil conditions under which the variety may be grown; the present description being of the variety as grown in the Central Valley of California.

I claim:

1. A plum tree of medium to small size, medium vigor, upright, open, vase-formed, hardy, and a regular and productive bearer of uniform, large to medium size, usually semi-freestone fruit having red skin and red flesh; the fruit being particularly characterized, in comparison to the Santa Rosa, by sizing more readily, by ripening approximately seven to ten days earlier, by more uniformity in size and color, and by firmer flesh.

No references cited.

ROBERT E. BAGWILL, Primary Examiner